United States Patent [19]
Parker

[11] Patent Number: 6,012,585
[45] Date of Patent: Jan. 11, 2000

[54] PORTABLE COLLAPSIBLE MEDICINE CONTAINER-CADDIE

[76] Inventor: Janet Marie Parker, 270 N. Broadway, Yonkers, N.Y. 10701

[21] Appl. No.: 08/805,354

[22] Filed: Feb. 24, 1997

[51] Int. Cl.[7] .................................................. A47B 73/00
[52] U.S. Cl. ........................... 206/570; 206/538; 211/72; 211/74; 211/75; 220/480
[58] Field of Search ..................... 206/528, 538, 206/570–572, 370; 211/72, 74, 75; 220/480–482; 312/209, 245, 259

[56] References Cited

U.S. PATENT DOCUMENTS

| | | | |
|---|---|---|---|
| D. 103,127 | 2/1937 | Schwartz | 211/74 |
| 503,233 | 10/1893 | Marshall . | |
| 723,964 | 3/1903 | Wilson | 211/74 |
| 862,771 | 8/1907 | Taylor | 206/570 |
| 1,254,639 | 1/1918 | Lang . | |
| 1,497,456 | 6/1924 | List . | |
| 1,685,125 | 9/1928 | Einson . | |
| 1,687,138 | 10/1928 | Myers . | |
| 1,729,014 | 9/1929 | Scherotto . | |
| 1,731,950 | 10/1929 | Tanner . | |
| 2,012,117 | 8/1935 | Barron . | |
| 2,307,992 | 1/1943 | Calhoun et al. . | |
| 2,324,232 | 7/1943 | Pantalone . | |
| 2,355,206 | 8/1944 | Davidson, Jr. . | |
| 2,426,689 | 9/1947 | Hilton | 211/72 |
| 2,597,731 | 5/1952 | Hoy . | |
| 2,677,469 | 5/1954 | Ebert . | |
| 2,688,408 | 9/1954 | Binggely et al. | 211/72 |
| 2,797,815 | 7/1957 | Gorman . | |
| 2,914,184 | 11/1959 | Dgetluck . | |
| 2,940,710 | 6/1960 | Adams . | |
| 3,464,567 | 9/1969 | Gowdy et al. | 211/74 |
| 3,983,976 | 10/1976 | Taylor | 220/481 |
| 4,160,570 | 7/1979 | Bridges | 220/482 |
| 4,194,617 | 3/1980 | Bandell . | |
| 4,560,072 | 12/1985 | Burrell | 211/75 |
| 4,570,805 | 2/1986 | Smith . | |
| 4,907,705 | 3/1990 | Waldeck | 211/72 |
| 5,213,220 | 5/1993 | McBride . | |
| 5,312,000 | 5/1994 | Bass | 211/74 |

*Primary Examiner*—Jim Foster

[57] ABSTRACT

A caddie for sickroom use for storing medicine containers, thermometers, cups and the like comprising a base, a back panel which supports the rear edge of a solid lower shelf, a second, upper shelf having multiple apertures formed therein which are preferably of annular cross-section having diameters slightly greater than the diameter of the standard size medication containers, but less than the diameter of the threaded caps which are placed upon the medicament containers. Apertures also can be provided suitable for placing a standard size thermometer in an upright position, and a larger one to hold a drinking cup and such. Below the apertured shelf is the solid shelf and below that is the base of the container which base is bordered on the sides by upwardly extending panels, and on the back by the upwardly extending back of panel, and a low front panel. The rear wall of the caddie on the rear face may have hooks for mounting the caddie on a wall or the like. The device can be made from cardboard or plastic blanks.

5 Claims, 9 Drawing Sheets

PORTABLE COLLAPSIBLE MEDICINE CONTAINER-CADDIE

BACKGROUND OF THE INVENTION

1. Field of the Invention

The present invention is concerned with a portable caddie or small storage container for storing medicines and various utensils commonly used by persons taking medications and those caring for such a person.

The present invention relates to a device for storing in a convenient and easily accessible manner a plurality of medicine containers, thermometers and other related items typically used by a person generally in a sickroom environment or elsewhere when they require repetitive periodic medications, determination of the temperature and means for holding liquid medicines and other items normally utilized by an ill person such as tissues, lozenges and the like.

The invention concerns an affordable, portable, foldable, paperboard, plastic, or similar material medication storage container or storage caddie.

The container provides an organized convenient storage arrangement for standard medication containers and commonly used utensils such as thermometer, measuring spoon, paper cups, tissues, and the like. In addition, the medicine container of the present invention is provided with means to suspend or hang the medicine storage container from the bed or other adjacent furniture of the person, or on a wall adjacent to the patient's bed or in similar location and to properly secure against unwanted moves, spilling and the like.

2. Prior Art

In the prior art there is a dearth of materials suitably designed to serve the function of a specific caddie for bedside use to store medications and also store other usual bedside accoutrements such as cups, thermometer, tissues, and the like.

Applicant's search of the prior art did not disclose any similar or equivalent type of bedside medicine container or caddie. The only prior art of any related nature seems to be display devices. There is no prior reference known by Applicant which shows any structure similar to the caddie disclosed and claimed in this application.

U.S. Pat. No. 2,940,710—Adam issued on Jun. 14, 1960 discloses a display stand base having a shelf 40 which folds into position and sides 4 and 6 which fold inwardly along fold lines 22 and 24 to collapse front 8 onto back 2 (see FIGS. 2 and 3).

U.S. Pat. 4,570,805—Smith issued on Feb. 18, 1986 discloses a display stand having sides which collapse inwardly to bring front $10^1$ and back $2^1$ together (see FIGS. 4 and 5).

In addition to these foregoing, references, the following references are also included as being of possible additional interest:

| U.S. Pat. | Name | Date of Issuance |
|---|---|---|
| 1,254,639 | Lang | 1/22/18 |
| 1,685,125 | Einson | 9/25/28 |
| 2,012,117 | Barron | 8/20/35 |
| 2,307,992 | Calhoun et al | 1/12/43 |
| 2,324,232 | Pantalone | 7/13/43 |
| 2,797,815 | Gorman | 7/2/57 |

-continued

| U.S. Pat. | Name | Date of Issuance |
|---|---|---|
| 2,914,184 | Dgetluck | 11/24/59 |
| 4,194,617 | Bandell | 3/25/80 |
| 1,497,456 | List | 6/10/24 |
| 1,731,950 | Tanner | 10/15/29 |
| 507,233 | Marshall | 10/24/1893 |
| 1,687,138 | Myers | 10/9/28 |
| 1,729,014 | Scherotto | 9/24/29 |
| 2,355,206 | Davidson, Jr. | 8/8/44 |
| 2,597,731 | Hoy | 5/20/52 |
| 2,677,469 | Ebert | 5/4/54 |
| 5,213,220 | McBride | 5/25/93 |

SUMMARY OF THE INVENTION

The container of the present invention provides an organized convenient storage arrangement for standard medication containers and commonly used sick-bed utensils such as thermometer, measuring spoon, paper cups, tissues and the like.

In addition, the medicine container of the present invention is provided with means to suspend or hang the medicine storage container from the bed or other furniture or on a wall adjacent to the bed, or other location, and to properly secure against unwanted moves, spilling and the like. Because the usual household medicine supplies are not normally kept set up in a bedroom or other part of the usual household and immediately available, it is desirable to provide a portable storage container such as the one disclosed herein the present application. It is further desirable that such an item, when not required, can be stored away readily, preferably, in very compact form.

It is one of the features of the present invention that the storage caddie or container of this invention, in a preferred embodiment, be manufactured as essentially a one piece blank with preformed folding lines and securing means to hold the components in the shape of the desired container structure.

In its broadest aspects, the invention of the present application provides a medicine container-caddie for use in a sickroom or similar environment wherein it can be placed on a supporting surface or hung or otherwise suspended from a vertical surface such as a wall by means of self-contained hooks or other securing means.

The caddie of the present invention comprises a base, a back panel which supports the rear edge of a solid lower shelf, a second, upper shelf having multiple apertures formed therein which are preferably of annular cross-section having diameters slightly greater than the diameter of the standard size medication containers, but less than the diameter of the threaded caps which are placed upon the medicament containers. Apertures also can be provided suitable for placing a standard size thermometer in an upright position, and a larger one to hold a drinking cup and such.

Below the apertured shelf is the solid shelf and below that is the base of the container which base is bordered on the sides by upwardly extending panels, and on the back by the upwardly extending back of panel, and a low front panel.

In a preferred embodiment of the invention, the caddie is collapsible by being foldable at certain joints and can be collapsed and stored in a flat folded condition.

The rear wall of the caddie of the present invention is generally formed as a standing generally rectangular panel with the longest sides rising upwardly from the rectangular base. The upper portion preferably may be shaped for decorative purposes, to signal its use as sickroom equipment in the form of a capped medicine jar container, as illustrated in the accompanying drawing.

Figure 1:
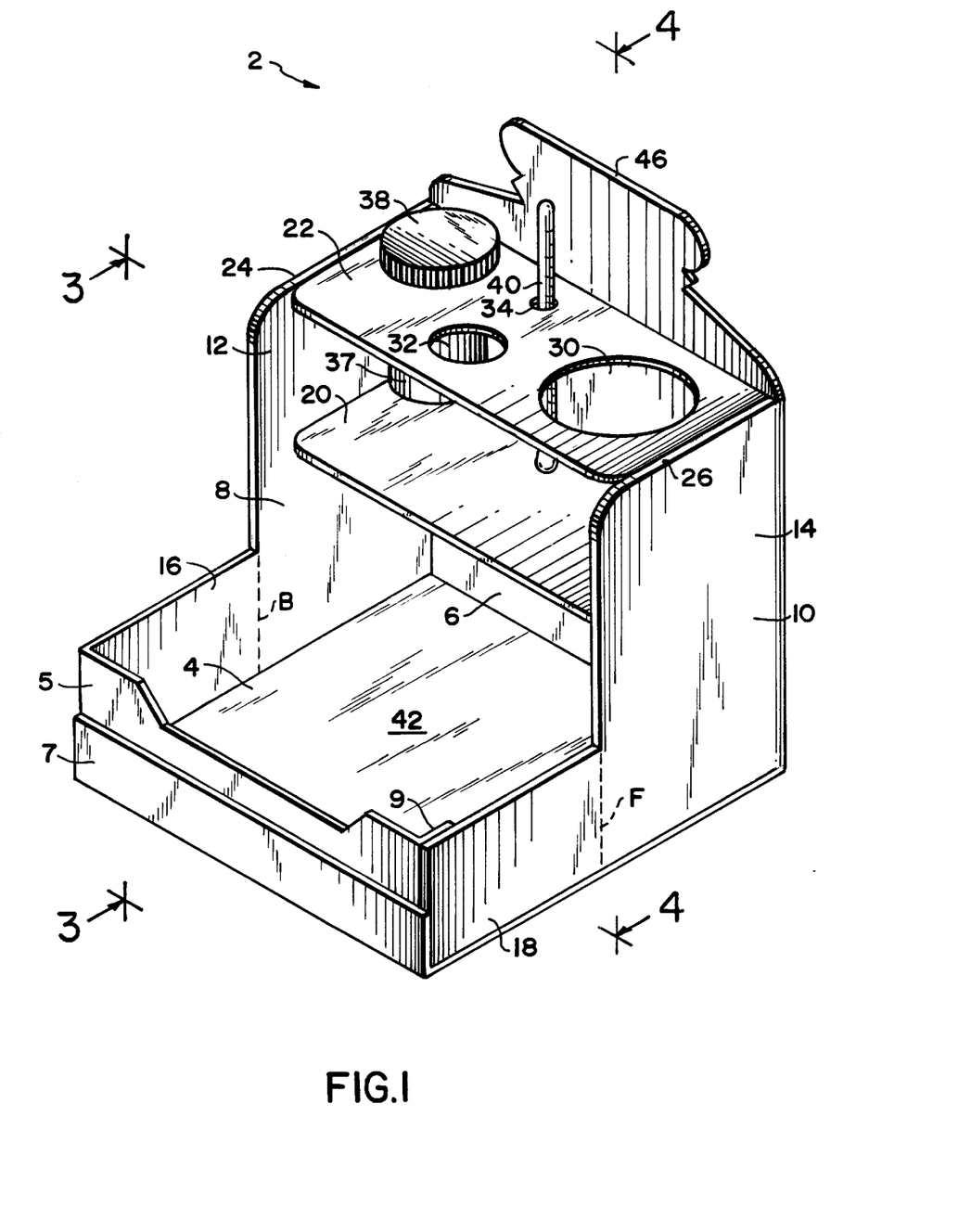
FIG. 1 is an perspective view of an assembled first embodiment of the invention.
Figure 2:
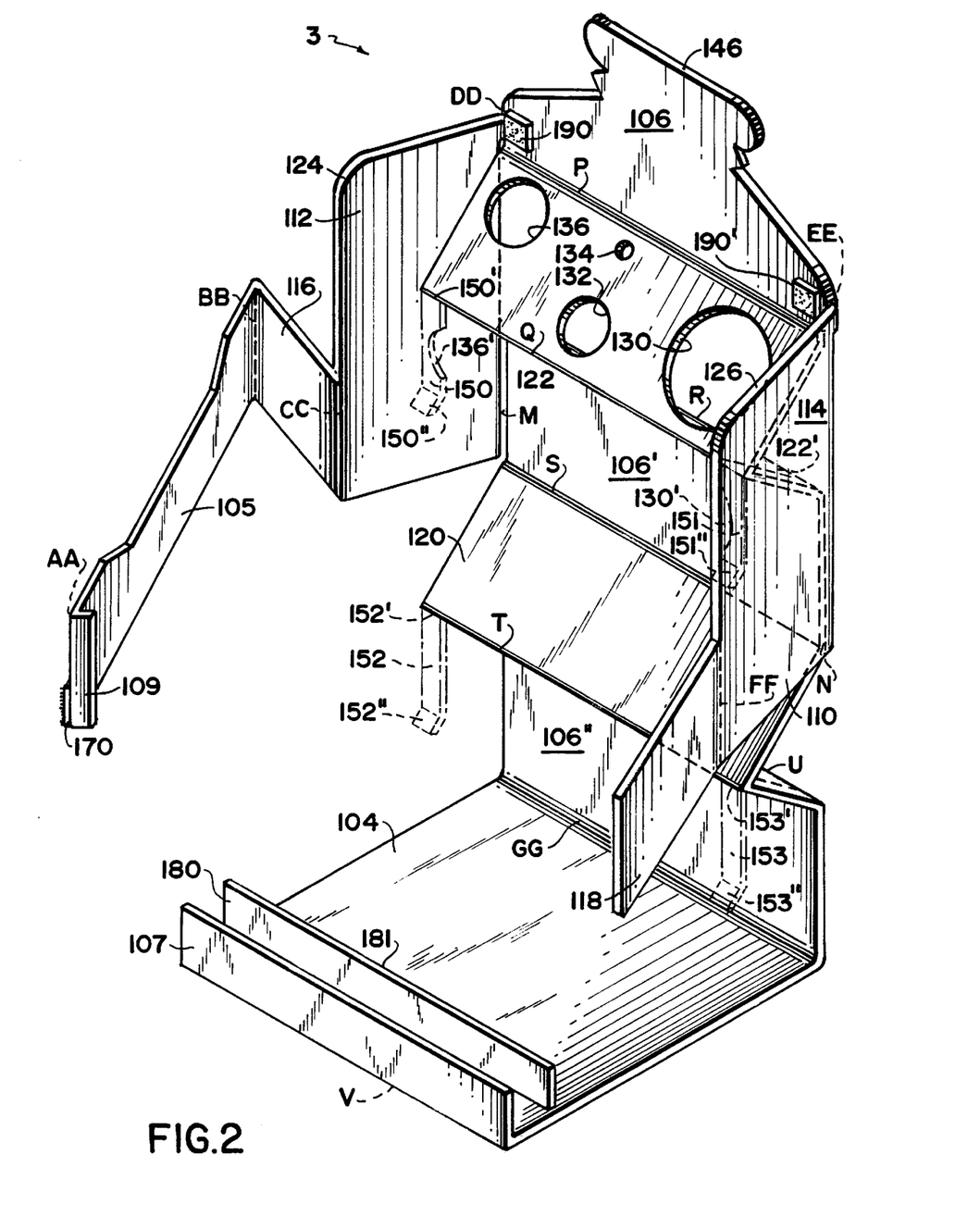
FIG. 2 is a perspective view of a second embodiment of the device prior to assembly.

It is apparent that the device of the present invention can be made from cardboard or plastic blanks and cut and folded to the shape illustrated, or can be made in component parts to be assembled by conventional plastic molding or fastening means into the form such as shown in FIGS. 1 and 2.

Because the device of the present invention may be formed of paperboard stock and folded flat in a preferred embodiment, it is also suitable as a promotional item for drug companies or local drug stores to use to display advertising on the panels as well as cautions and directions in taking certain drugs, and other useful information for a person under medical care and taking medication.

While the device of the illustrated embodiment shown is a collapsible structure, the basic structure also may be fabricated from various materials including heavy cardboard stock, wood, plastic, and the like and rigidly constructed as well.

BRIEF DESCRIPTION OF THE DRAWING

In the accompanying drawing which forms a part of this application illustrated representative embodiments of the invention are disclosed.

ILLUSTRATIVE SPECIFIC EMBODIMENTS

Referring to the accompanying drawing a first embodiment of the present invention is illustrated in FIGS. 1, 1A, 1B, 3, 4, and 7.

Figure 4:
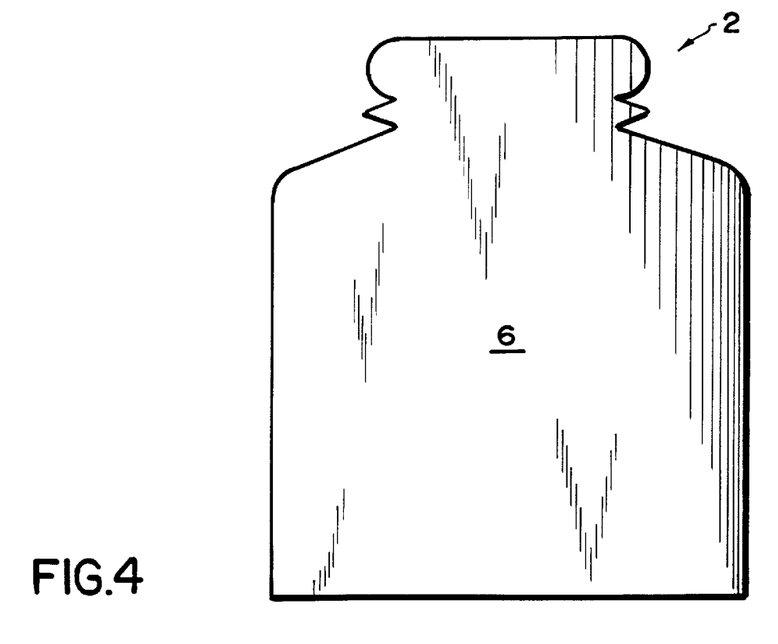
FIG. 4 is a rear plan view thereof taken along lines 4—4 of FIG. 1.

The device of the present invention is indicated in general at 2 and comprises a rectangular base panel 4, back panel 6 rising from the base 4 and joined to two sides 8 and 10 respectively. The rear panel 6 as shown in FIG. 4 in silhouette form looks like a medicine container.

The side panels 8 and 10 have rear sections 12 and 14 that rise to the full height of the caddie 2 and lower sections 16 and 18 to a height just under first or lower shelf 20 so that access may be had to items that are stored directly on the base panel 4. As shown intermediate the base 4 and the top shelf 22 is the second shelf 20 that is solid and within the upper reaches of the side panels 8 and 10.

Even with a top edges 24 and 26 of the sides 8 and 10 is the apertured top shelf 22 running from the right 8 to left wall 10 and having a number of apertures formed therein and indicated by 30, 32, 34, and 36. The larger apertures are of a diameters corresponding to slightly larger than the diameter of standard medicine dispenser containers 37 and less than the diameter of the screw caps 38 of such containers.

With this arrangement any number of various sized medicine dispensing containers 37 may be conveniently stored on the top shelf 22 and when it is desired to use them to dispense medications, they are simply grasped by the twist top and removed from the apertured storage. A smaller aperture 34 is provided for storing a thermometer 40. Other apertures may be provided for storing other items if desirable. A larger aperture 30 for storing a 5–7 ounce drinking cup is also provided.

Items such as tissues, spoons, containers, vials, and the like may be stored in the lower storage compartment indicated in general by the numeral 42 and defined by the base 4, sides 8 and 10, back 6, and front 5 panel walls.

The cabinet or dispenser shown in FIG. 1 may be constructed using materials such as wood, plastic, for instance Lexan, or the like by any known method.

Figure 1A:
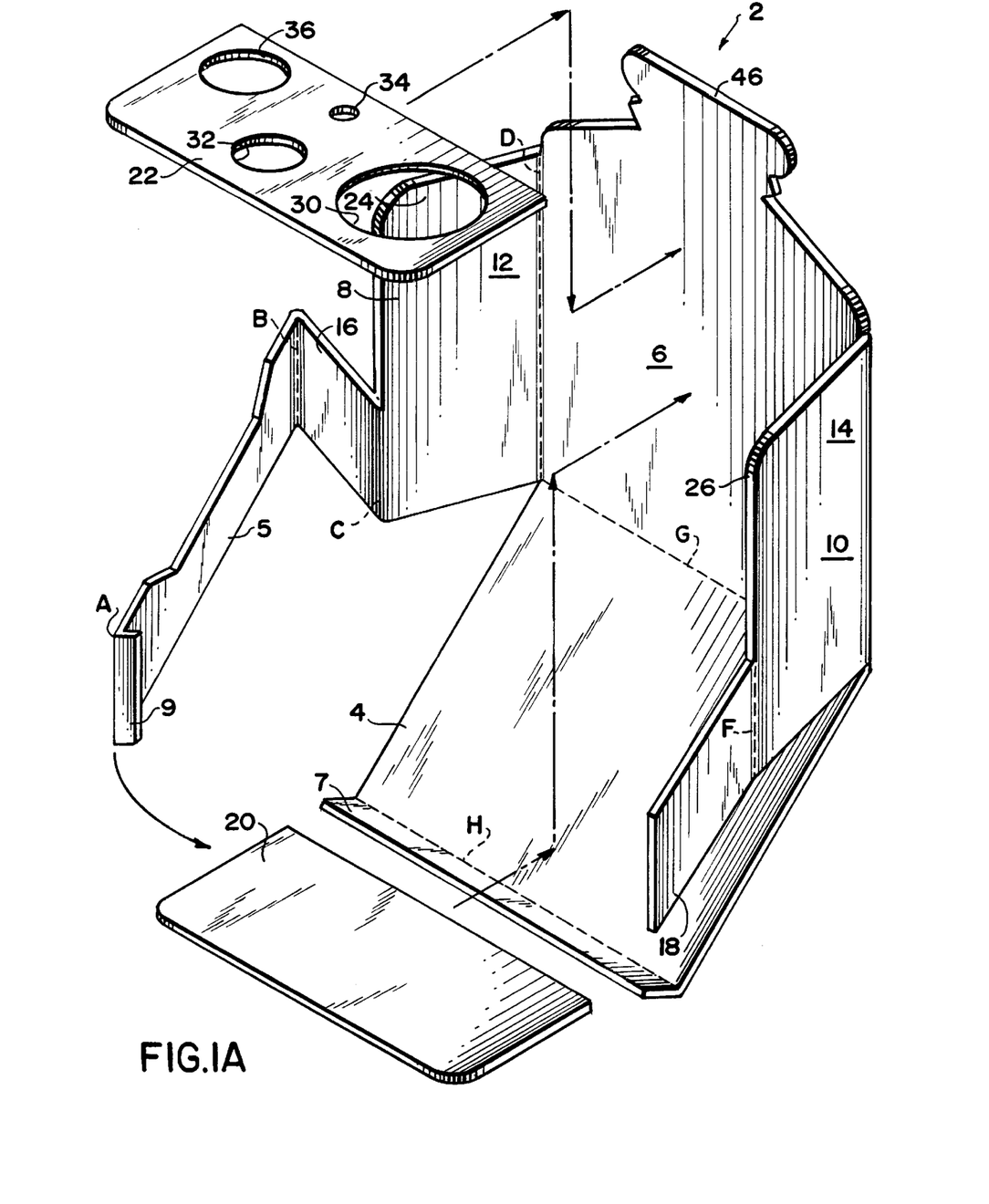
FIG. 1A is a perspective view of a typical blank from which to assemble the mdicine container caddie of FIG. 1 of the present invention.
Figure 1B:
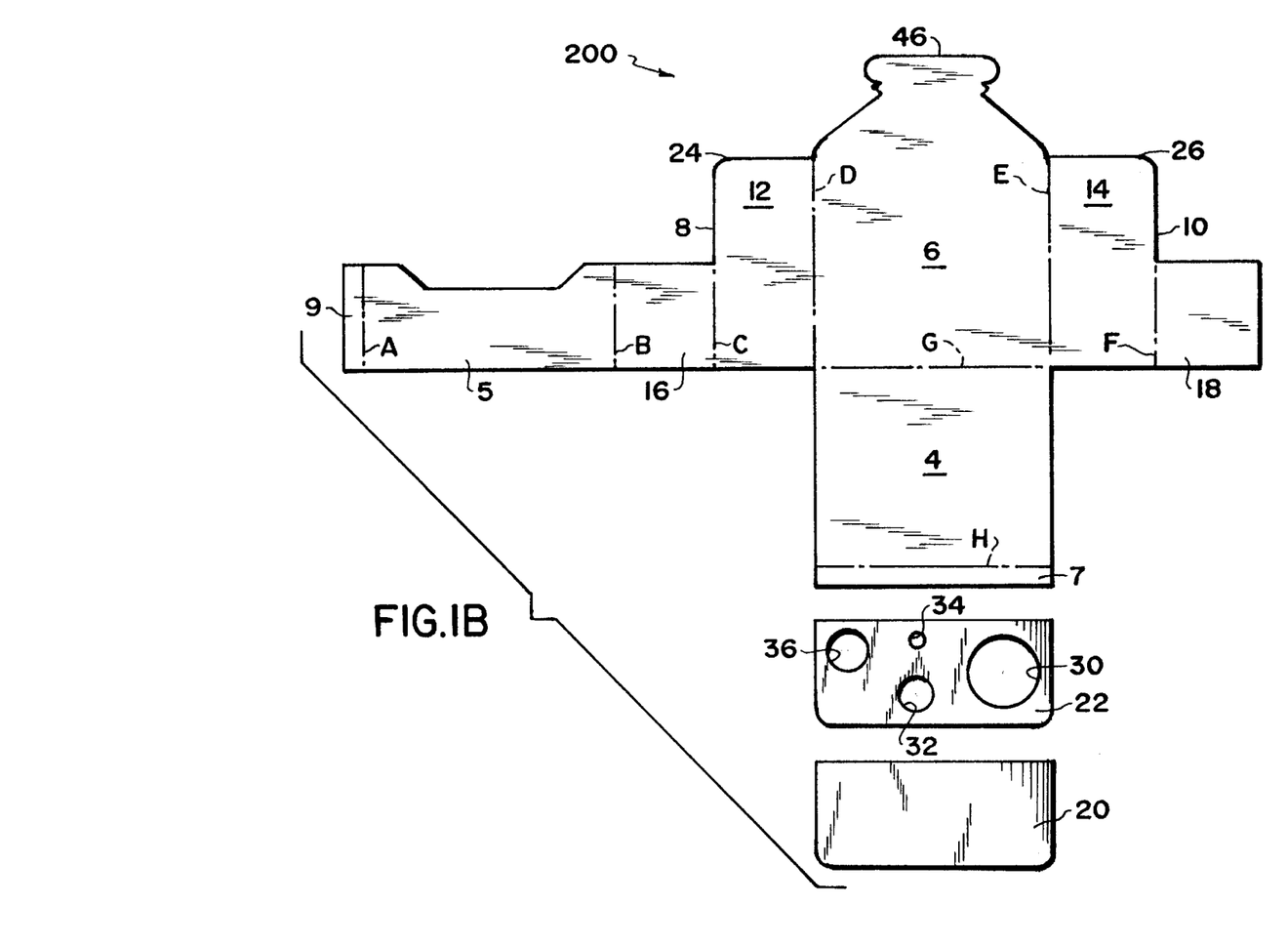
FIG. 1B is a plan view of the blank for the device shown in FIGS. 1 and 1A.

FIG. 1-A shows the assembly of the caddie shown in FIG. 1 from a paperboard blank 200. The broken lines indicated by the letters A through H designate embossed fold lines in the blank 200. The shelves 20 and 22 in this embodiment are stamped out separately.

Figure 7:
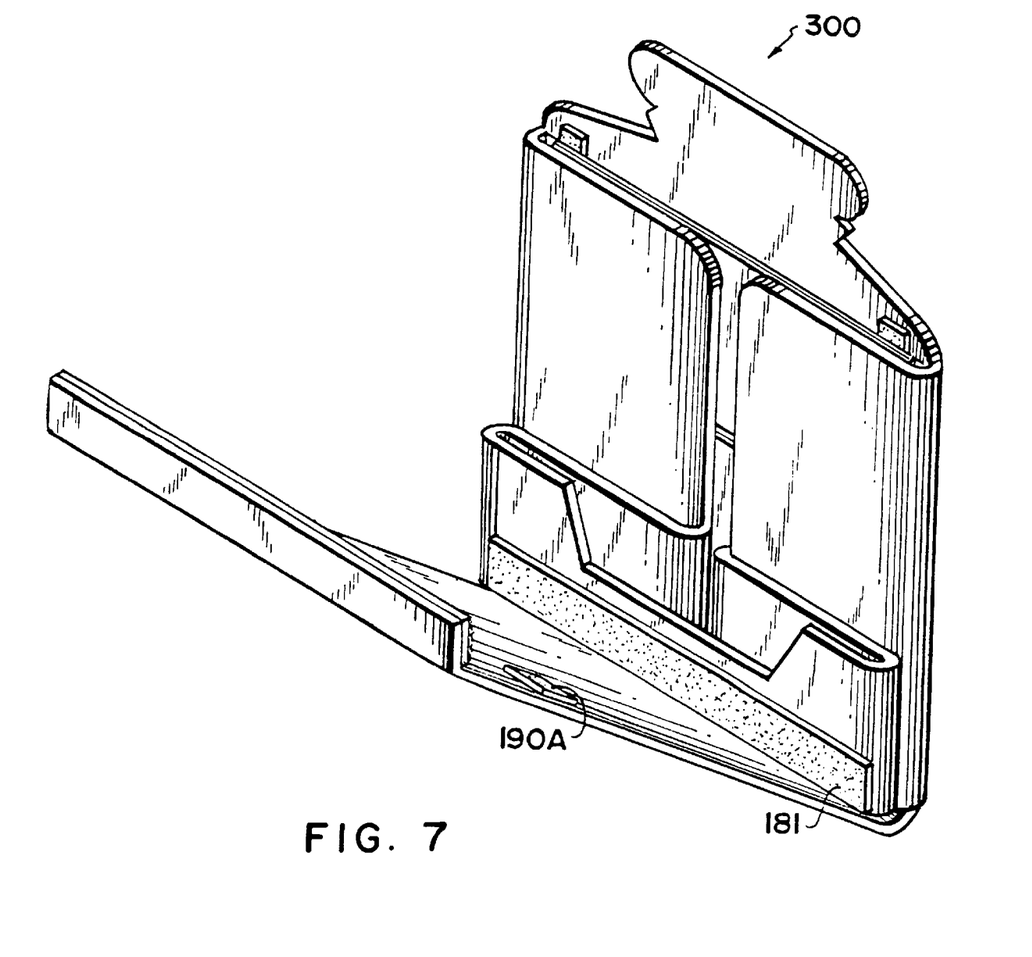
FIG. 7 shows the rear of the device of FIG. 1 folded.

The blank 200 can be folded up into a compact package as illustrated in FIG. 7.

The blank 200 is assembled by bending the panels on the fold lines A–H as shown in FIG. 1A. The tab 9 is adhered against side panel 18 as shown in FIG. 1. The tab 7 is glued to the front panel 5. The edges of the shelves 20 and 22 in turn are adhered with adhesive to the back 6 and sides 12 and 14. The assembly of a caddie 3 of the present invention from a modified blank 300 is shown in FIGS. 2, 2A, 5 and 6.

In this case the blank 100 is a single integral blank of one piece 300.

In this case the single blank includes both the shelves as part of the blank and it is even more compact than the prior blank package. The panels and other parts common to the first embodiment are generally indicated in this embodiment with numerals which are the same as those used for the first embodiment except they begin with the additional integer 1; thus panel 112 is analogous to panel 12 and base 104 is analogous to base 4 and so on. In the case of common fold lines, the fold lines letters of the first embodiment are doubled in this embodiment. There are some additional parts and fold lines in this embodiment which will be explained in the following specific description.

Figure 2A:
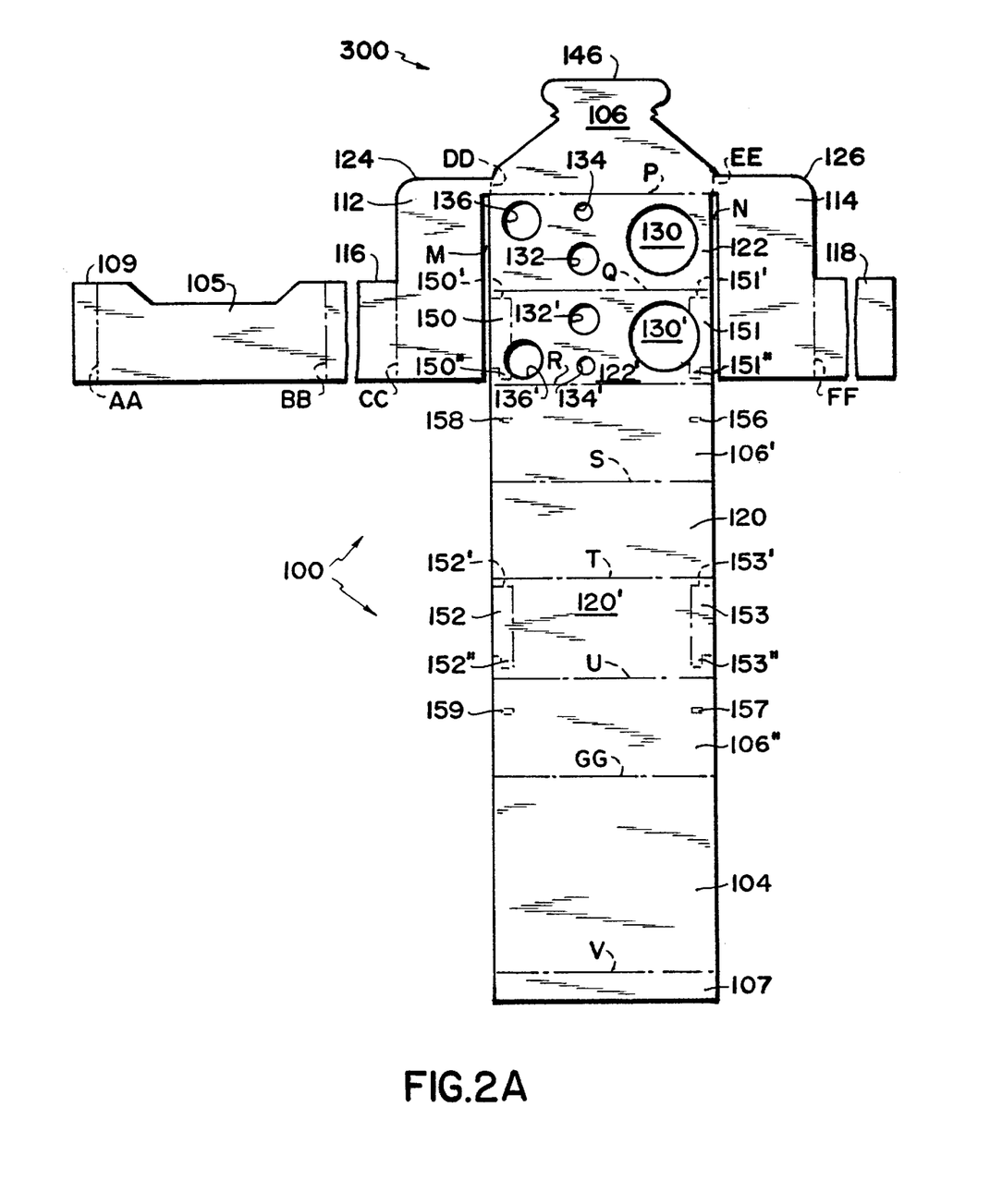
FIG. 2A is a plan view of flat stock for the assembly of the embodiment shown in FIG. 2 with punch outs and appropriate creases embossed on the paper board stock.
Figure 3:
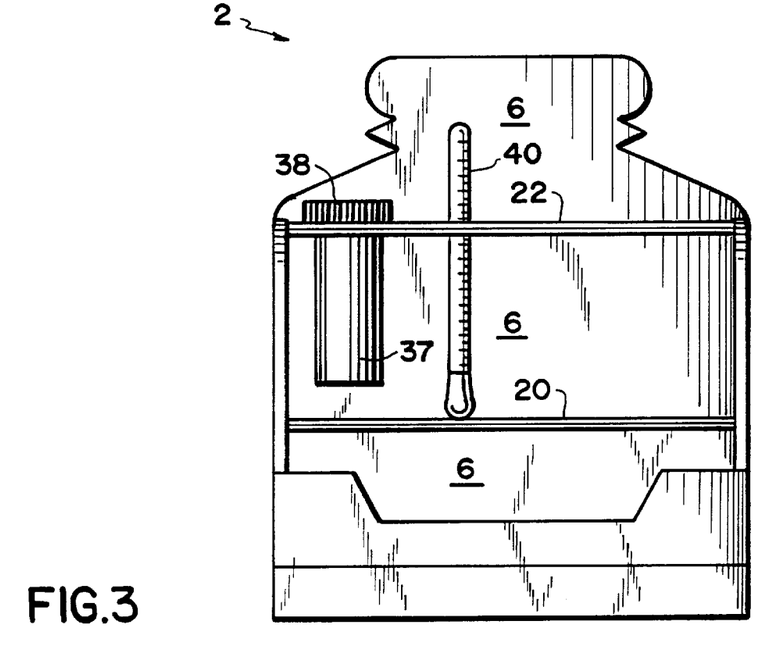
FIG. 3 is a front plan view of the device of FIGS. 1, 1A, taken along lines 3—3 of FIG. 1.

Referring first to the flat blank 300 shown in the FIG. 2A, it comprises the rectangular base panel 104, back panel comprised of sections 106, 106' and 106".

In the first embodiment, the portion of the rear 106 is shaped as indicated at 146 like the top of a medicine container. The side panels 108 and 110 have rear sections 112 and 114 that rise to the full height of the caddie, and lower sections 116 and 118 to the height under the first or lower shelf 120 and 122'. The top edges of the sides 108 and 110 are indicated by 124 and 126. The top shelf is comprised of panels 122 and 122' which are folded against each other along line P and extend from panel 106 along fold P and from panel 106' along fold R; the lower shelf is comprised of panels 120 and 120' which are folded along line T to form that shelf and extend panel 106' and 106" along fold line S and U respectively.

Slots M and N allow bending along fold lines P, Q and R, so that the panels 122 and 122' may be folded against each other to form the upper shelf and that matches up the apertures 130 and 130', 132 and 132', 134 and 134', and 136 and 136' in alignment with each other respectively. It should be noted in panels 120' and 122' of the end shelf that provision is made for tabs 150, 151 having extensions 150' and 151" respectively and they punch out to be fitted into apertures 156 and 158 respectively when the panels are folded over to form the upper shelf. Panel 160' forms the back wall between the upper and lower shelves 120 and 122 respectively. The panels 120 and 120' are folded against each other and the tear tabs 150 and 153 respectively with the end extension 152" and 150" pulled out. These are bent along the score lines 152$^1$ and 153$^1$ as indicated and are fitted into slots 157 and 159 respectively which slots punch out. The panel 106" forms the lower portion of the back wall and the base thereof is folded along the lines GG between it and the bottom panel 104. Fold line B is between the bottom 104 and the front connecting panel 107.

Figure 5:
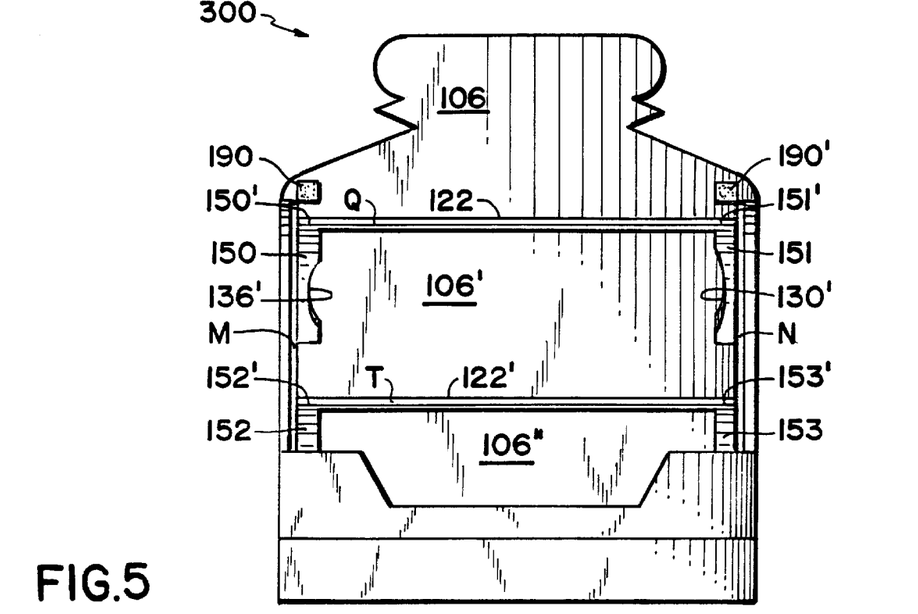
FIG. 5 is a front plan view of the device of FIGS. 2 and 2A.
Figure 6:
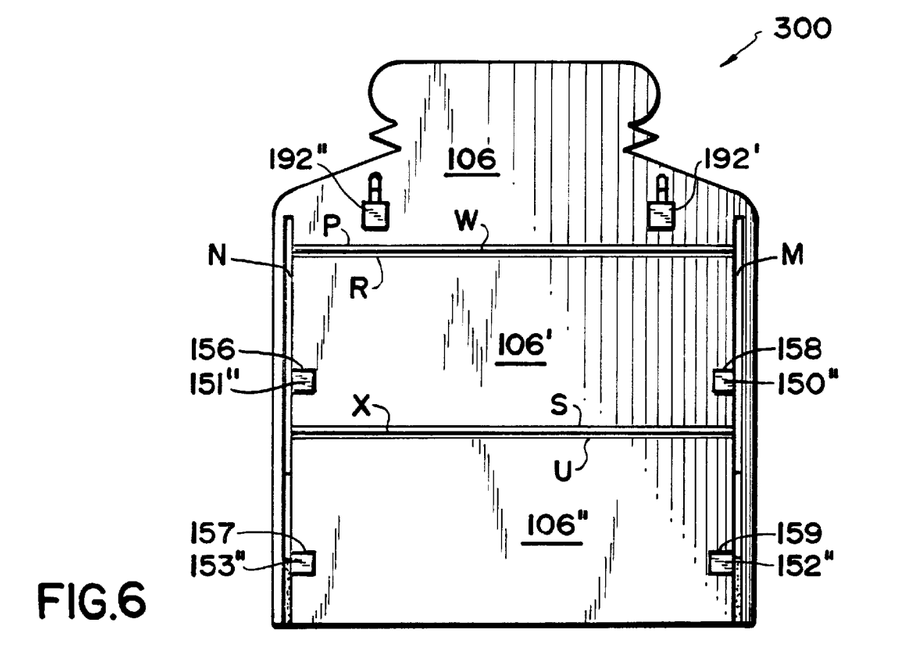
FIG. 6 is a back plan view thereof showing hanging means.

In FIG. 2A the space between the side panels 112 and 114 respectively and the center portion 106 is defined by the spaces M and N respectively. The caddie is assembled as indicated in FIG. 2 and results in the final caddie assemblage as shown in FIGS. 5 and 6, FIG. 5 is a view from the front, and FIG. 6 a view from the rear end.

The front panel 105 is formed between the corners' BB fold line and AA fold line. The extension 109 of front panel 105 is lapped over by low forward portion 118 of the panel 114. Adhered to the inside face of the panel 107 above fold V is a strip 180, the face part 181 of which is Velcro and this matches the Velcro on the strip 170 that is glued to the forward side of the panel 105.

Figure 8:
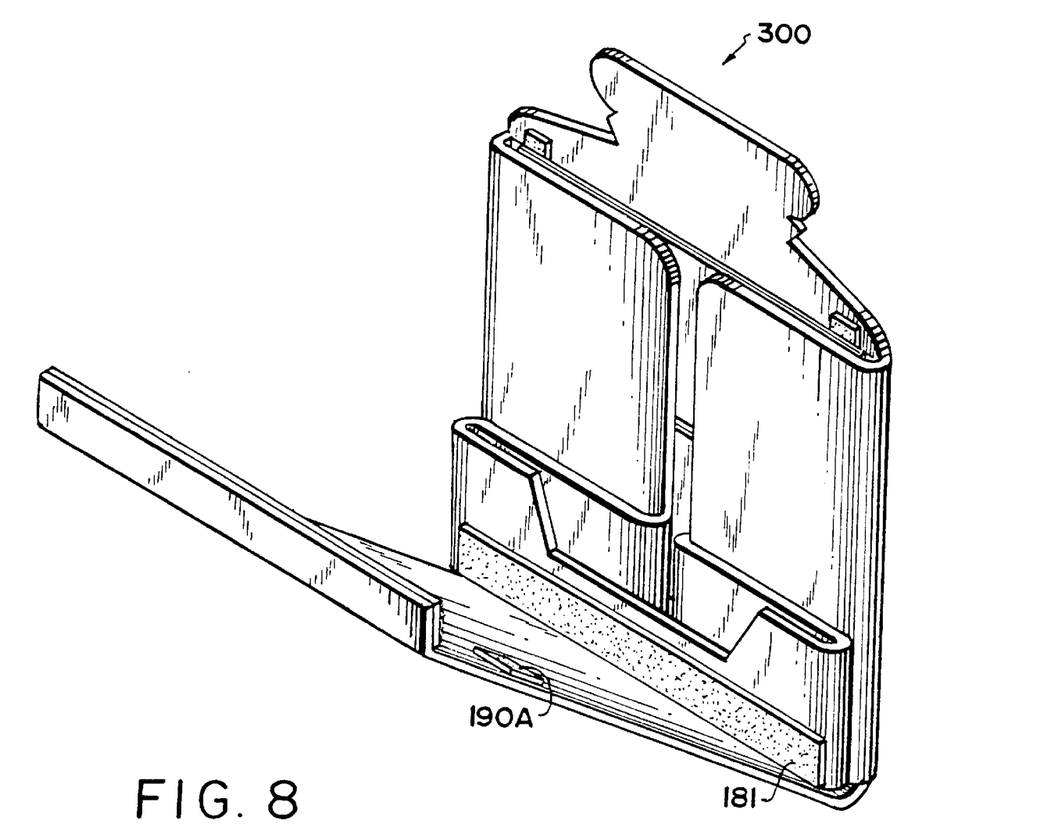
FIG. 8 is the device of FIG. 2 folded.

The shelf 120 is held in level position by the strips 152 and 153 the ends of which 152' and 153' fit into the slots 157 and 159 respectively. The Velcro strips indicated are glued on as well as strips 190 and 190' at the upper corners of the front face of the panel portion 106 cooperate with the panel face 181 when the device is folded as shown in FIG. 8.

The rear face 106A of panel 106 optionally may have hanging hooks 192 and 192' adhesively secured to it to provide means to hang the device on the wall or other vertical surface.

While the storage container of the present invention has been illustrated by embodiments which are collapsible and fold flat, the storage container may be constructed of a permanently erected style without diminishing its uniqueness and utility. It is then preferably constructed of plastic.

While the invention has been described by reference to illustrative embodiments, it is not intended that the novel device be limited thereby, but that modifications thereof are intended to be included as falling within the broad spirit and scope of the foregoing disclosure, the following claims and the appended drawings.

What is claimed is:

1. A portable, collapsible medication caddie adapted for storing medication containers and supplies and having the silhouette of a medicine container, said containers having a generally cylindrical shape, said caddie comprising a pair of opposed side panels, a front and rear panel foldably joined to said side panels, a closed base foldably joined to the lower edge of said rear panel, a lower horizontal shelf foldably joined to the rear panel and extending from said rear panel of said caddie and spaced from said front panel, a second upper shelf foldably joined to the rear panel and located higher than said lower shelf, said second shelf having a top surface and circular apertures formed therein with dimensions suitable for receiving and holding cylindrical medicine containers, and having other apertures adapted for storing a thermometer and drinking cup, said lower shelf adapted to support bases of said cylindrical containers, said rear panel extending upwardly above a top surface of said upper shelf, and a rear face on said rear panel, means for hanging said caddie vertically on a wall surface, said caddie being of a unitary construction and being foldable where the panels, sides and shelves are foldably joined to permit collapsing of the caddie to facilitate portability.

2. A caddie as claimed in claim 1 made of folded paperstock prefolded to be assembled into the shape of said caddie.

3. A caddie as claimed in claim 1 made of plastic.

4. A portable, collapsible medication caddie adapted for storing medication containers and supplies and having the silhouette of a medicine container, said containers having a generally cylindrical shape, said caddie comprising a pair of opposed side panels, a front and rear panel foldably joined to said side panels, a closed base foldably joined to the lower edge of said rear panel, a lower horizontal shelf mounted the rear panel and extending from said rear panel of said caddie and spaced from said front panel, a second upper shelf mounted to the rear panel and located higher than said lower shelf, said second shelf having a top surface and circular apertures formed therein with dimensions suitable for receiving and holding cylindrical medicine containers, and having other apertures adapted for storing a thermometer and drinking cup, said lower shelf adapted to support bases of said cylindrical containers, said rear panel extending upwardly above a top surface of said upper shelf, and a rear face on said rear panel, means for hanging said caddie vertically on a wall surface, said caddie being of a unitary construction and being foldable along where the panels and sides are joined to permit collapsing of the caddie to facilitate portability.

5. A portable, collapsible medication caddie adapted for storing medication containers and supplies and having the silhouette of a medicine container in accordance with claim 1 further including:

a first front panel foldably joined to the base and a second front panel foldably joined to one of sides, said panels being in engagement with each other; and, a first front strip having a plurality of plastic hooks thereon mounted on the first panel and a second strip mounted on a side panel having a plurality of plastic loops thereon whereby the strips engage one another to hold the caddie in place and to permit ready collapsing of the caddie.

\* \* \* \* \*